US012752036B2

(12) United States Patent
Kohler Riedi et al.

(10) Patent No.: US 12,752,036 B2
(45) Date of Patent: Oct. 6, 2026

(54) WOUND DRESSING MATERIAL AND METHODS OF MAKING AND USING THE SAME

(71) Applicant: Solventum Intellectual Properties Company, Maplewood, MN (US)

(72) Inventors: Petra L. Kohler Riedi, Minneapolis, MN (US); Saurabh Batra, Minneapolis, MN (US); Naimul Karim, Maplewood, MN (US); Joseph J. Stoffel, Hastings, MN (US); Rajan B. Bodkhe, Woodbury, MN (US); Joseph A. Dunbar, Woodbury, MN (US)

(73) Assignee: Solventum Intellectual Properties Company, Eagan, MN (US)

( * ) Notice: Subject to any disclaimer, the term of this patent is extended or adjusted under 35 U.S.C. 154(b) by 420 days.

(21) Appl. No.: 17/925,558

(22) PCT Filed: Jun. 3, 2021

(86) PCT No.: PCT/IB2021/054872
§ 371 (c)(1),
(2) Date: Nov. 15, 2022

(87) PCT Pub. No.: WO2021/250513
PCT Pub. Date: Dec. 16, 2021

(65) Prior Publication Data

US 2023/0190988 A1 Jun. 22, 2023

Related U.S. Application Data

(60) Provisional application No. 63/038,280, filed on Jun. 12, 2020.

(51) Int. Cl.
*A61L 15/42* (2006.01)
*A61L 15/24* (2006.01)
(Continued)

(52) U.S. Cl.
CPC ............. *A61L 15/425* (2013.01); *A61L 15/24* (2013.01); *A61L 15/46* (2013.01); *A61L 15/62* (2013.01)

(58) Field of Classification Search
CPC ................ A61F 13/022; A61F 13/0289; A61F 13/00063; A61F 13/00987;
(Continued)

(56) References Cited

U.S. PATENT DOCUMENTS 3,678,933 A * 7/1972 Moore .................... A61F 13/34 604/371
3,849,241 A 11/1974 Butin et al.
(Continued)

FOREIGN PATENT DOCUMENTS

EP 1341561 B1 12/2001
WO 2013101702 A1 7/2013
(Continued)

OTHER PUBLICATIONS

Polyvinyl Acetate Resins [online], [retrieved on Sep. 22, 2024]. [Retrieved from the Internet <URL:https://museumservicescorporation.com/products/polyvinyl-acetate-resins-ayac (Year: 2024).*
(Continued)

*Primary Examiner* — Alireza Nia
*Assistant Examiner* — Andrew Jun-Wai Mok

(57) ABSTRACT

A wound dressing material comprises a porous flexible foam core, a wound-contact scrim, and an antimicrobial layer. The wound-contact scrim comprises water-sensitive fibers comprising a copolymer comprising divalent hydroxyethylene monomer units and divalent dihydroxybutylene monomer units. The antimicrobial layer is sandwiched between the porous flexible foam core and the wound-contact scrim. The
(Continued)

wounds dressing material may be contacted with an exposed surface of a wound. A method of making the wound dressing material is also disclosed.

18 Claims, 1 Drawing Sheet

(51) Int. Cl.

| | |
|---|---|
| ***A61L 15/46*** | (2006.01) |
| ***A61L 15/62*** | (2006.01) |
| ***C08L 29/04*** | (2006.01) |

(58) Field of Classification Search

CPC ......... A61F 13/01029; A61F 13/01017; A61L 2300/404; A61L 15/225; A61L 15/24; A61L 15/42; A61L 15/46; A61L 15/425; A61L 15/44; A61L 15/62; D04H 1/4309; D04H 1/732

See application file for complete search history.

(56) References Cited

U.S. PATENT DOCUMENTS

| | | | | |
|---|---|---|---|---|
| 3,867,939 | A * | 2/1975 | Moore | A61F 7/02 607/104 |
| 4,118,531 | A | 10/1978 | Hauser | |
| 4,307,143 | A | 12/1981 | Meitner | |
| 4,707,398 | A | 11/1987 | Boggs | |
| 5,951,993 | A | 9/1999 | Scholz et al. | |
| 6,168,800 | B1 * | 1/2001 | Dobos | A61L 15/26 424/443 |
| 6,494,974 | B2 | 12/2002 | Riddell | |
| 6,548,727 | B1 | 4/2003 | Swenson | |
| 6,872,311 | B2 | 3/2005 | Koslow | |
| 10,604,631 | B2 | 3/2020 | Boswell | |
| 10,604,632 | B2 | 3/2020 | Boswell | |
| 2003/0135172 | A1 * | 7/2003 | Whitmore | A61L 15/60 604/359 |
| 2004/0259445 | A1 * | 12/2004 | Hilfenhaus | A61L 15/46 442/41 |
| 2005/0266760 | A1 | 12/2005 | Chhabra et al. | |
| 2005/0287891 | A1 | 12/2005 | Park | |
| 2006/0096911 | A1 | 5/2006 | Brey et al. | |
| 2009/0061719 | A1 | 3/2009 | Shibutnai et al. | |
| 2011/0247839 | A1 | 10/2011 | Lalouch et al. | |
| 2013/0165880 | A1 * | 6/2013 | Amos | A61L 15/20 514/159 |
| 2014/0336557 | A1 * | 11/2014 | Durdag | A61L 15/26 604/319 |
| 2016/0263272 | A1 * | 9/2016 | Zhuang | A61F 13/15211 |
| 2018/0290440 | A1 | 10/2018 | Boswell | |
| 2018/0291162 | A1 | 10/2018 | Boswell | |
| 2019/0256809 | A1 | 8/2019 | Pinyayev et al. | |

FOREIGN PATENT DOCUMENTS

| | | | |
|---|---|---|---|
| WO | 2020261035 | A1 | 12/2020 |
| WO | 2021059188 | A1 | 4/2021 |
| WO | 2021084354 | A1 | 5/2021 |

OTHER PUBLICATIONS

Moore, et al. The Swelling of Cotton in Water: A Microscopical Study. Sage Journal, Abstract, vol. 20, Issue 9, Sep. 1950, Abstract [online], [retrieved on Sep. 22, 2024]. Retrieved form the Internet <URL:<https://journals.sagepub.com/doi/10.1177/004051755002000904 (Year: 1950).*

International Search Report received for PCT International Application No. PCT/IB2021/054872, mailed on Jul. 28, 2021, 4 pages.

Wente, "Superfine Thermoplastic Fibers", Industrial and Engineering Chemistry, Aug. 1956, vol. 48, No. 8, pp. 1342-1346.

* cited by examiner

WOUND DRESSING MATERIAL AND METHODS OF MAKING AND USING THE SAME

CROSS REFERENCE TO RELATED APPLICATIONS

This application is a national stage filing under 35 U.S.C. 371 of PCT/IB2021/054872, filed Jun. 3, 2021, which claims the benefit of U.S. Application No. 63/038,280, filed Jun. 12, 2020, the disclosure of which is incorporated by reference in its/their entirety herein.

TECHNICAL FIELD

The present disclosure broadly relates to antimicrobial wound dressing materials, to processes suitable for the preparation of such materials, and to the use of such materials as wound dressings.

BACKGROUND

Traditionally, wet-to-dry gauze has been used to dress wounds. Dressings that create and maintain a moist environment, however, are now typically considered to provide optimal conditions for wound healing. Indeed, highly hydrophilic and absorbent wound dressing materials are part of the rapidly growing advanced wound care market. Absorbent wound dressing products are popular with clinicians and are made of materials which absorb and hold moisture at the wound site. The most common materials used in these products are alginate and carboxymethyl cellulose.

There is a continuing need for materials and articles to facilitate wound healing.

SUMMARY

Advantageously, the present disclosure provides antiseptic wound dressing materials that provide a moist environment while providing antimicrobial protection, even in the presence of cationic antiseptics.

In one aspect, the present disclosure provides a wound dressing material comprising:

- a porous flexible foam core having first and second opposed major sides;
- a first wound-contact scrim comprising first water-sensitive fibers, wherein the first water-sensitive fibers comprise a first copolymer comprising divalent hydroxyethylene monomer units and divalent dihydroxybutylene monomer units; and
- a first antimicrobial layer sandwiched between the first major side of the porous flexible foam core and the first wound-contact scrim.

In another aspect, the present disclosure provides a method of using a wound dressing material, the method comprising contacting the first wound-contact scrim of a wound dressing material according to the present disclosure with an exposed surface of a wound.

In yet another aspect, the present disclosure provides a method of making a wound dressing material, the method comprising laminating sequential layers:

a) a first wound-contact scrim comprising water-sensitive fibers, wherein the water-sensitive fibers comprise a first copolymer comprising divalent hydroxyethylene monomer units and divalent dihydroxybutylene monomer units;

b) a first antimicrobial layer; and c) a porous flexible foam core.

As used herein:

- the term "scrim" refers to a lightweight highly porous fabric that may be woven or nonwoven;
- the term "water-sensitive" means water swellable and/or water-soluble; and
- the term "wound" refers to an injury to a subject (e.g., a mammal) which involves a break in the normal skin barrier exposing tissue below, which is caused by, for example, lacerations, surgery, burns, damage to underlying tissue such as pressure sores, or poor circulation. Wounds are understood to include both acute and chronic wounds.

Features and advantages of the present disclosure will be further understood upon consideration of the detailed description as well as the appended claims.

Figure 1:
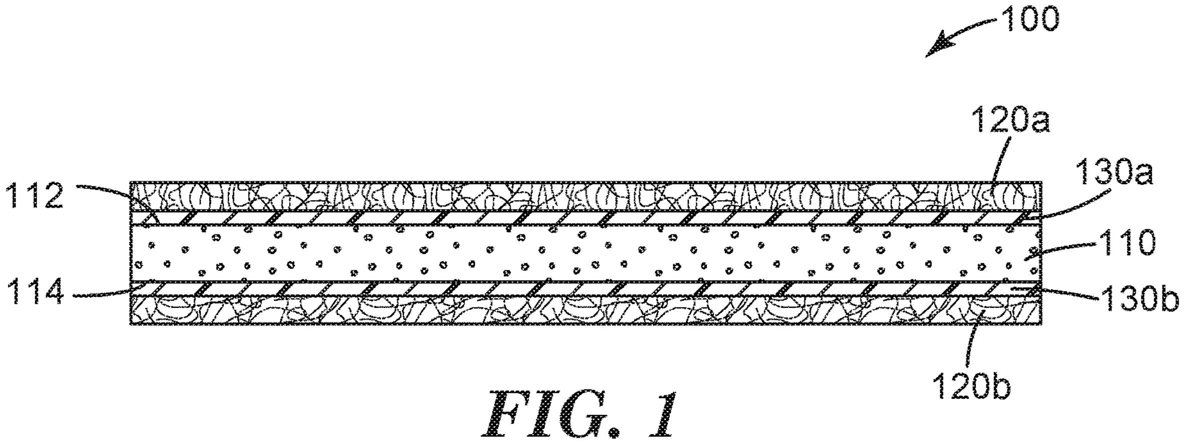
FIG. 1 is a schematic side view of an exemplary wound dressing material 100 according to the present disclosure.

Repeated use of reference characters in the specification and drawings is intended to represent the same or analogous features or elements of the disclosure. It should be understood that numerous other modifications and embodiments can be devised by those skilled in the art, which fall within the scope and spirit of the principles of the disclosure. The figures may not be drawn to scale.

DETAILED DESCRIPTION

Referring now to FIG. 1, wound dressing material 100 comprises porous flexible foam core 110 having first and second opposed major sides (112, 114). First wound-contact scrim **120*a* comprises water-sensitive fibers comprising a first copolymer divalent hydroxyethylene monomer units and divalent dihydroxybutylene monomer units. First antimicrobial layer 130*a* is sandwiched between first major side 112 of porous flexible foam core 110 and first wound-contact scrim 120*a*. Optional second wound-contact scrim 120*b* comprises second water-soluble fibers comprising a second copolymer comprising divalent hydroxyethylene monomer units and divalent dihydroxybutylene monomer units. Optional second antimicrobial layer 130*b* is sandwiched between second major side 114 of porous flexible foam core 110 and optional second wound-contact scrim 120*b***.

The porous flexible foam core can be a porous flexible polymeric foam, although this is not a requirement. The porous flexible foam core can be crosslinked or uncrosslinked. Useful porous flexible foams are preferably open-cell foams, although perforated or slit closed cell-foams may also be useful, for example. The porous flexible foam core should generally be at least sufficiently flexible to easily conform to anatomical features associated with wounds.

Preferably, the porous flexible foam core is absorbent, and more preferably it comprises an absorbent, substantially non-swellable foam. In this context, an "absorbent" foam is one that is capable of absorbing saline water, and hence, exudate from a wound. Preferably, suitable porous flexible foam cores are those that can absorb greater than 250%, more preferably at least about 500%, and most preferably at least about 800%, by weight aqueous saline solution based on the dry weight of the porous flexible foam core. Typically, these values are obtained using a saline absorbency test in which a dry, weighed sample is immersed for 30 minutes at 37° C. in phosphate-buffered saline containing 0.9 wt. % NaCl.

The porous flexible foam cores can be of a wide range of thicknesses. Preferably, they are at least about 0.5 millimeter, and more preferably at least about 1 millimeter thick. Preferably, they are no greater than about 80 millimeters, and more preferably no greater than about 30 millimeters thick.

Furthermore, they can include one or more layers tailored to have the desired properties. These layers can be directly bonded to each other or bonded together with adhesive layers, for example, as long as the overall properties of the wound dressing, as described herein, are met. Optionally, disposed between these layers can be one or more layers of polymeric netting or nonwoven, woven, or knit webs for enhancing the physical integrity of the porous flexible foam core. Suitable open cell foams preferably have an average cell size (typically, the longest dimension of a cell, such as the diameter) of at least about 30 microns, more preferably at least about 50 microns, and preferably no greater than about 800 microns, more preferably no greater than about 500 microns, as measured by scanning electron microscopy (SEM) or light microscopy. Such porous flexible foam cores when used in dressings of the present disclosure allow transport of fluid and cellular debris into and within the foam. Preferably, the porous flexible foam core includes a synthetic polymer that is adapted to form a conformable open cell foam that absorbs the wound exudate.

Exemplary porous flexible foam cores can comprise porous foams made of polyolefin (e.g., polyethylene or polypropylene), polystyrene, polyurethane, polyacrylate, polyester (e.g., polylactic acid), polycarbonate, polyamide, carboxylated butadiene-styrene rubbers, and combinations thereof. These materials are commercially available and/or can be made by known extrusion methods such as polymer (gas) saturation or inclusion of a foaming agent. Polyurethane foams are often preferred.

A particularly preferred foam is a polyurethane, available under the trade designation POLYCRIL 400 from Fulflex, Inc, Middleton, Rhode Island. Although suitable foams may be hydrophilic per se, they are preferably hydrophobic and treated to render them more hydrophilic, for example with surfactants such as nonionic surfactants, e.g., the oxypropylene-oxyethylene block copolymers available under the trade designation PLURONIC from BASF Wyandotte, Mount Olive, New Jersey. Use of foams, or surfactants incorporated therein, that possess a hydrophilic surface reduces the tendency for the exudate to coagulate rapidly in the foam. This helps to keep the wound in a moist condition even when production of exudate has ceased from the wound. One preferred porous flexible foam core can be obtained as TEGADERM foam wound dressing from 3M Company.

Further details concerning suitable polymer foams can be found in U.S. Pat. No. 6,548,727 (Swenson), the disclosure of which is incorporated herein by reference.

The first and optional second wound-contact scrims may be the same or different. They comprise water-sensitive fibers that comprise first and optionally second copolymers (which may be the same or different), each respective copolymer comprising divalent hydroxyethylene monomeric units (i.e.,

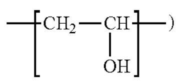

and divalent dihydroxybutylene monomer units. In preferred embodiments, the divalent dihydroxybutylene monomer units comprise 3,4-dihydroxybutan-1,2-diyl monomer units (i.e.,

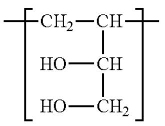

monomer units). Optionally, but typically, the copolymer furthers comprise acetoxyethylene divalent monomeric units (i.e., (i.e.,

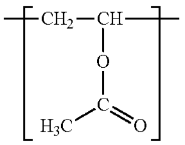

monomer units). The copolymer may be obtained by copolymerization of vinyl acetate and 3,4-dihydroxy-1-butene followed by partial or complete saponification of the acetoxy groups to form hydroxyl groups.

Alternatively, in place of 3,4-dihydroxy-1-butene, a carbonate such as

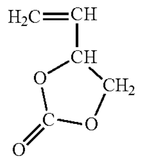

can also be used. After copolymerization, this carbonate may be hydrolyzed simultaneously with saponification of the acetate groups. In another embodiment, in place of 3,4-dihydroxy-1-butene, an acetal or ketal having the formula:

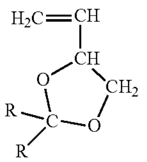

where each R is independently hydrogen or alkyl (e.g., methyl or ethyl). After copolymerization, this carbonate may be hydrolyzed simultaneously with saponification of the acetate groups, or separately. The copolymer can be made according to known methods or obtained from a commercial supplier, for example.

Commercially available copolymers may include those available under the trade designation Nichigo G-Polymer (Nippon Gohsei Synthetic Chemical Industry, Osaka, Japan), a highly amorphous polyvinyl alcohol, that is believed to have divalent monomer units of hydroxyethylene, 3,4-dihydroxybutan-1,2-diyl, and optionally acetoxyethylene. Nippon Gohsei also refers to Nichigo G-Polymer by the chemical name butenediol vinyl alcohol (BVOH). Exemplary materials include Nichigo G-Polymer grades AZF8035W, OKS-1024, OKS-8041, OKS-8089, OKS-8118, OKS-6026, OKS-1011, OKS-8049, OKS-1028, OKS-1027, OKS-1109, OKS-1081, and OKS-1083. These copolymers are believed to have a saponification degree of 80 to 97.9 mole percent, and further contain an alkylene oxide adduct of a polyvalent alcohol containing 5 to 9 moles of an alkylene oxide per mole of the polyvalent alcohol. These materials have melt-processing properties that are suitable for forming melt-blown, spunbond webs, and melt spun fibers which can be converted to staple fibers and further converted into air-laid nonwovens.

The first and optional second wound-contact scrims may contain secondary fibers in addition to the copolymer fibers. Suitable secondary fibers may include all fibers listed for the porous flexible foam core hereinbefore. Preferred secondary fibers include fibers comprising polyvinyl alcohol(s), carboxymethyl cellulose, rayon, cotton, cellulose acetate, hydrophilic thermoplastic polyurethane(s), chitosan, polyacrylic acid, sulfonated cellulose, cellulose ethyl sulfonate, alginate, or any combination thereof.

Methods of forming the wound-contact scrim(s) will depend on the type of fiber web formed, but will be well-known to those of skill in the textile arts. Suitable methods may include airlaying and/or carding of staple fibers followed by needletacking to densify and strengthen the fiber web; melt-blown; spunbond; and wet-laid processes. In some embodiments, nonwoven fiber webs (e.g., the porous flexible foam core and/or the wound-contact scrim(s) may be made by air-laying of staple fibers. Air-laid nonwoven fiber webs may be prepared using equipment such as, for example, that available as a RANDO WEBBER from Rando Machine Company of Macedon, New York. In some embodiments, a type of air-laying may be used that is termed gravity-laying, as described e.g., in U. S. Pat. Application Publication 2011/0247839 (Lalouch). Nonwoven staple fiber webs may be densified and strengthened, for example, by techniques such as crosslapping, stitchbonding, needletacking, chemical bonding, and/or thermal bonding.

Melt-blowing methods are well-known in the art. As used herein, the term "melt-blowing" refers to a process in which fibers are formed by extruding a molten thermoplastic material through a plurality of fine, usually circular, die capillaries into a high velocity gas (e.g., air) stream which attenuates the molten thermoplastic material and forms fibers, which can be to microfiber diameter, such as less than 10 microns in diameter. Thereafter, the melt-blown fibers are carried by the gas stream and are deposited on a collecting surface to form a web of random melt-blown fibers. Such a process is disclosed, for example, in U.S. Pat. No. 3,849,241 (Butin et al.); U.S. Pat. No. 4,307,143 (Meitner et al.); and U.S. Pat. No. 4,707,398 (Wisneski et al.).

Fibers in the wound-contact scrims may be staple and/or continuous, preferably at least substantially continuous. For example, the first and/or optional second wound-contact scrims may comprise a meltblown fiber web or a spunbond fiber web. Fibers in the wound-contact scrims may have any average diameter and/or length, preferably from 2 to 200 microns and more preferably 2 to 100 microns.

The wound-contact scrim may have any basis weight, but in many embodiments, it is preferably in the range of 5 to 150 gsm, more preferably 10 to 100 gsm, and more preferably 10 to 75 gsm.

Optionally, wound-contact scrims may further comprise at least one of addition of a plurality of staple fibers or addition of particulates. Suitable methods are described in U.S. Pat. No. 4,118,531 (Hauser), U.S. Pat. No. 6,872,315 (Koslow), and U.S. Pat. No. 6,494,974 (Riddell); and in U. S. Pat. Appl. Publ. Nos. 2005/0266760 (Chhabra et al.), 2005/0287891 (Park), and 2006/0096911 (Brey et al.). In other exemplary embodiments, the optional particulates may be added to a nonwoven fiber stream by air laying a fiber web, adding particulates to the fiber web (e.g., by passing the web through a fluidized bed of particulates), optionally with post heating of the particulate-loaded web to bond the particulates to the fibers.

The antimicrobial layers provide effective topical antimicrobial activity and thereby treat and/or prevent a wide variety of afflictions. For example, they can be used in the treatment and/or prevention of afflictions that are caused, or aggravated by, microorganisms (e.g., Gram positive bacteria, Gram negative bacteria, fungi, protozoa, *mycoplasma*, yeast, viruses, and even lipid-enveloped viruses) on skin. Particularly relevant organisms that cause or aggravate such afflictions include *Staphylococcus* spp., *Streptococcus* spp., *Pseudomonas* spp., *Enterococcus* spp., and Esherichia spp., bacteria, as well as herpes virus, *Aspergillus* spp., *Fusarium* spp., *Candida* spp., as well as combinations thereof. Particularly virulent organisms include *Staphylococcus aureus* (including resistant strains such as Methicillin Resistant *Staphylococcus aureus* (MRSA), *Staphylococcus epidermidis, Streptococcus pneumoniae, Enterococcus faecalis*, Vancomycin Resistant *Enterococcus* (VRE), *Pseudomonas aeruginosa, Escherichia coli, Aspergillus niger, Aspergillus fumigatus, Aspergillus clavatus, Fusarium solani, Fusarium oxysporum, Fusarium chlamydosporum, Candida albicans, Candida glabrata, Candida krusei*, and combinations thereof.

In some embodiments, the antimicrobial layers may be a surface coating (e.g., a paste or gel) on either or both of the porous flexible foam core or a wound-contact scrim or it may be a freestanding layer (e.g., a film).

In some embodiments, antimicrobial layers, when provided as a free thin film (i.e., not as a coating on a substrate) have a basis weight in the range of 20 to 700 gsm, more preferably in the range of 75 to 600 gsm, and more preferably in the range of 100 to 500 gsm, are typically flexible and can be deformed without breaking, shattering, or flaking of the antimicrobial layer.

Each antimicrobial layer comprises at least one antimicrobial compound. Exemplary antimicrobial compounds include antibiotics (e.g., amoxicillin, bacitracin zinc, doxycycline, cephalexin, ciprofloxacin, clindamycin, metronidazole, azithromycin, sulfamethoxazole, trimethoprim, or levofloxacin), and antiseptics such as chlorhexidine and its salts (e.g., chlorhexidine digluconate and chlorhexidine diacetate), antimicrobial lipids, phenolic antiseptics, cationic antiseptics, iodine and/or an iodophor, peroxide antiseptics, antimicrobial natural oils, alkane-1,2-diols having 6 to 12 carbon atoms, silver, silver salts and complexes, silver oxide, copper, copper salts, and combinations thereof. Preferred antimicrobial compounds include antimicrobial quaternary amine compounds (e.g., benzalkonium chloride) and salts thereof, cationic surfactants (e.g., cetylpyridinium chloride or cetyltrimethylammonium bromide), polycationic compounds such as octenidine or a salt thereof, biguanide compounds (e.g., chlorhexidine, polyhexamethylenebiguanide (PHMB) or a salt thereof, 1,2-organic diols having 6 to 12 carbon atoms (e.g., 1,2-octanediol), antimicrobial fatty acid monoester compounds, and combinations thereof.

Wound dressing materials according to the present disclosure may have broad-spectrum antimicrobial activity. However, the wound dressing materials are typically sterilized; for example, by sterilized by a variety of industry standard techniques. For example, it may be preferred to sterilize the wound dressing materials in their final packaged form using electron beam. It may also be possible to sterilize the sample by gamma radiation, nitrogen dioxide sterilization and/or heat. Other forms of sterilization may also be used. It may also be suitable to include preservatives in the formulation to prevent growth of certain organisms. Suitable preservatives include industry standard compounds such as parabens (e.g., methylparaben, ethylparaben, propylparaben, isopropylparaben, or isobutylparaben); 2 bromo-2 nitro-1,3-diol; 5 bromo-5-nitro-1,3-dioxane, chlorbutanol, diazolidinyl urea; iodopropyl butyl carbamate, phenoxyethanol, halogenated cresols, methylchloroisothiazolinone; and combinations thereof.

Many preferred antimicrobial layers comprise an effective amount of a polycarboxylic acid chelator compound, alone or in combination with any of the foregoing antimicrobial compounds. The amount is effective to prevent growth of a microorganism and/or to kill microorganisms on a surface to which the composition is contacted.

In certain embodiments, the polycarboxylic acid chelator compound, whether aliphatic, aromatic, or a combination thereof, comprises at least two carboxylic acid groups. In certain embodiments, the polycarboxylic acid chelator compound, whether aliphatic, aromatic or a combination thereof, comprises at least three carboxylic acid groups. In certain embodiments, the polycarboxylic acid chelator compound, whether aliphatic or aromatic, comprises at least four carboxylic acid groups.

Polycarboxylic acid-containing chelator compounds suitable for use in antimicrobial layer include aliphatic polycarboxylic acids, aromatic polycarboxylic acids, compounds with both one or more aliphatic carboxylic acids and one or more aromatic carboxylic acids, salts thereof, and combinations of the foregoing. Nonlimiting examples of suitable polycarboxylic acid-containing chelator compounds include citric acid, glutaric acid, glutamic acid, maleic acid, succinic acid, tartaric acid, malic acid, ethylenediaminetetraacetic acid, phthalic acid, trimesic acid, and pyromellitic acid.

Preferred salts include those formed from monovalent inorganic bases and include cations such as $K^+$, $Na^+$, $Li^+$, and $Ag^+$, and combinations thereof. In some compositions polyvalent bases may be appropriate and include cations such as $Ca^{2+}$, $Mg^{2+}$, $Zn^{2+}$, Alternatively, the salt of the polycarboxylic acid may be formed using an organic base such as a primary, secondary, tertiary, or quaternary amine.

In many embodiments, the polycarboxylic acid-comprising chelator compound may be present in the antimicrobial layer at relatively high concentrations (on a weight basis) while the composition remains surprisingly nonfrangible. The minimum effective amount of chelator compound in the antimicrobial layer is related to the number of carboxyl groups in the chelator compound. For example, succinic acid (with two carboxyl groups) is generally more efficacious than glutamic acid having the same number of carboxylic acid groups since in glutamic acid carboxyl group forms a zwitterion with an amino group.

Mucic acid is another example with 2 carboxyl groups. Mucic acid is not as efficacious as succinic acid since the carboxyl groups are further apart and sterically hindered. In certain embodiments, efficacy of the composition can be improved by using thicker (greater basis weight) antimicrobial layers. Efficacy may depend on the amount of acid in the antimicrobial layer as well as the total amount (mass) of the antimicrobial layer. Thus, in some embodiments, the chelator compound comprises at least about 5, 10, 15, 20, 25, 30, 35, 40, 45, 50, 55, or even at least 60 percent by weight of an essentially solvent-free antimicrobial layer. The term "essentially solvent-free" is understood to mean that the antimicrobial layer has been processed to remove most of the solvent (e.g., water and/or organic solvent) or has been processed in such a way that no solvent (e.g., water and/or organic solvent) was required. This is generally the article for sale, e.g., before it has been applied to a patient. Generally, solvents are relatively volatile compounds having a boiling point at one atmosphere pressure of less than 150° C. Solvent may be used to process (e.g., coat or film-form) the antimicrobial layer, but is preferably substantially removed to produce the final article for sale. For example, certain precursor compositions used to form the antimicrobial layer are first combined with water as a vehicle to form a solution, emulsion, or dispersion. These precursor compositions are coated and dried on a substrate (e.g., a release liner, the porous flexible foam core, and/or the wound-contact scrim(s)) such that the water content of the antimicrobial layer is less than 10 percent by weight, preferably less than 5 percent by weight, and more preferably less than 2 percent by weight.

In some embodiments, the chelator compound comprises up to about 15, 20, 25, 30, 35, 40, 45, 50, 55, or even up to about 60 percent by weight of the essentially dry antimicrobial layer on a weight basis.

In certain embodiments, wherein the polycarboxylic acid-comprising chelator compound comprises two aliphatic carboxylic acid groups (e.g., succinic acid), the chelator compound comprises at least about 10 percent by weight of the essentially dry antimicrobial layer on a weight basis. In certain embodiments, wherein the polycarboxylic acid-comprising chelator compound comprises three aliphatic carboxylic acid groups (e.g., citric acid), the chelator compound comprises at least about 10 percent by weight of the essentially dry antimicrobial layer on a weight basis. In certain embodiments, wherein the polycarboxylic acid-comprising chelator compound comprises four aliphatic carboxylic acid groups (e.g., ethylenediaminetetraacetic acid), the chelator compound comprises at least about 5 percent by weight of the essentially dry antimicrobial layer on a weight basis.

When preparing antimicrobial layers of the present disclosure, the polycarboxylic acid-containing chelator compound may be dissolved and/or dispersed in a water-soluble plasticizer component and optionally a solvent such as water. The plasticizer component has a boiling point greater than 105° C. and has a molecular weight of less than 5000 daltons. Preferably, the plasticizer component is a liquid at 23° C. Typically, but not necessarily, the plasticizer component is the most abundant solvent in the antimicrobial layer in which the polycarboxylic acid-containing chelator compound is dissolved and/or dispersed. In certain embodiments wherein water is used to prepare the antimicrobial layer, substantially all of the water is subsequently removed (e.g., after the antimicrobial layer has been coated onto a substrate).

In certain embodiments, the chelator compound comprises an aliphatic and/or aromatic polycarboxylic acid, in which two or more of the carboxylic groups are available for chelation without any zwitterionic interaction. Although potential zwitterionic interactions (e.g., such as in L-glutamic acid) may decrease antimicrobial efficacy relative to similar compounds (e.g., glutaric acid, succinic acid) that do not comprise α-amino groups, such zwitterionic compounds also exhibit antimicrobial activity. In addition, two or more carboxylic acid groups in the polycarboxylic acid-containing chelator compounds should be disposed in the chelator compound in sufficient proximity to each other or the compound should be capable of folding/conforming to bring the carboxylic acids sufficiently close to facilitate chelation of metal ions.

In certain embodiments, the chelator compound comprises an aliphatic polycarboxylic acid or a salt thereof, an aromatic polycarboxylic acid or a salt thereof, or a combination thereof. In certain embodiments, the chelator compound comprises an aliphatic portion. In certain embodiments, the chelator compound comprises an aliphatic portion. The carboxylic acids may be disposed on the aliphatic portion and/or on the aromatic portion. Nonlimiting examples of chelator compounds that comprise an aliphatic portion with a carboxylic acid group disposed thereon and an aromatic portion with a carboxylic acid group disposed therein include 3-(2-carboxyphenyl) propionic acid, 3-(4-carboxyphenyl) propionic acid, and 4-[(2-carboxyphenyl)amino]benzoic acid.

In certain embodiments, efficacy of the antimicrobial layer can be improved by depositing a higher amount of dried antimicrobial layer. Efficacy is dependent on concentration of chelator compound in the antimicrobial layer as well as total amount of the antimicrobial layer.

The antimicrobial layer may contain plasticizer. Suitable plasticizers may include, for example, glycerol, a polyglycerol having 2-20 glycerin units, polyglycerols partially esterified with $C_1$-$C_{18}$ alkylcarboxylic acids having at least two free hydroxyl groups (e.g., hexaglycerol monolaurate, decaglycerol monolaurate, polyglyceryl-6 caprate, polyglyceryl-4 oleate, polyglyceryl-10 trilaurate and the like), polyethylene oxide, polyethylene glycol, polyethylene glycols initiated by any of the glycols discussed herein such as polyethylene glycol glyceryl ether, propylene glycol, dipropylene glycol, tripropylene glycol, 2-methyl-1,3-propanediol, sorbitol, dimethylisosorbide, pentaerythritol, trimethylolpropane, ditrimethylolpropane, a random ethylene oxide/propylene oxide (EO/PO) copolymer or oligomer, a block EO/PO copolymer or oligomer, and combinations thereof.

Plasticizer may be present in the antimicrobial layer at relatively high concentrations (on a weight basis). In some embodiments, plasticizer comprises at least about 10 percent by weight of the antimicrobial layer. In some embodiments, plasticizer comprises at least about 10, 15, 20, 25, 30, 35, 40, 45, 50, 55, 60, 65, 70, or even at least 75 percent by weight of the antimicrobial layer. In certain embodiments, the plasticizer component can act as a humectant. Advantageously, this can maintain a moist environment in a wound to help promote healing of wound tissue.

Advantageously, the relatively high concentration of plasticizer and/or water-soluble or water-dispersible polymer in the antimicrobial layer can function as a controlled-release modulator that facilitates delivery of the antimicrobial(s) over an extended period of time. In some embodiments, the plasticizer component can also function as an antimicrobial component.

Antimicrobial layers according to the present disclosure are preferably solid at 25° C. In certain embodiments, the antimicrobial layer may comprise a solvent having a normal boiling point of less than or equal to 100° C. Nonlimiting examples of such solvents include water and lower ($C_2$-$C_5$) alcohols. Preferably, before use, the antimicrobial layer comprises very little solvent (e.g., less than or equal to about 10 percent by weight) having a normal boiling point of less than or equal to 100° C. In some embodiments, the antimicrobial layer comprises less than 5 percent by weight, less than 4 percent by weight, less than 3 percent by weight, less than 2 percent by weight, or even less than 1 percent by weight (by weight) of a solvent having a normal boiling point of less than or equal to 100° C. In certain embodiments, the antimicrobial layer may be substantially free (before use) of such solvents or any compounds having a normal boiling point of less than 100° C.

In many preferred embodiments, the antimicrobial layer(s) comprise a water-soluble or water-dispersible polymer as a binder. The water-soluble or water-dispersible polymer has a Tg greater than or equal to 20° C. In use, the polymer can function to form the antimicrobial layer into a cohesive shape such as a film while also absorbing wound exudate and to maintain a moist environment that can facilitate healing of the tissue at a wound site.

Exemplary water-soluble and/or water-dispersible polymers that are suitable for use in a antimicrobial layer according to the present disclosure include polyvinylpyrrolidone; polyvinyl alcohol; copolymers of vinyl alcohol; polybutylenediol; polysaccharides (e.g., starch); guar gum; locust bean gum; carrageenan; hyaluronic acid; agar; alginate; tragacanth; gum arabic; gum karraya; gellan; xanthan gum; hydroxyethylated, hydroxypropylated, and/or cationic derivatives of the foregoing; modified cellulose polymers (e.g., hydroxyethylcellulose, hydroxypropyl methylcellulose, carboxymethylcellulose, or cationic cellulose such as polyquaterium 4); copolymers of polyvinylpyrrolidone and vinyl acetate; water-soluble and water-swellable polyacrylates (e.g., based on hydroxyethyl (meth)acrylate, hydroxypropyl (meth) acrylate, (meth)acrylic acid, (meth)acrylamide, PEG (meth)acrylates, methyl (meth)acrylate), and combinations thereof. As used herein the term "(meth)acryl" refers to acryl and/or methacryl. In certain embodiments, the water-soluble or water-dispersible polymers can comprise a polyquaternium polymer.

In some embodiments, the water-soluble or water-dispersible polymer comprises at least about 5 percent by weight of the antimicrobial layer. In some embodiments, the water-soluble or water-dispersible polymer comprises up to about 65 percent by weight of the antimicrobial layer.

The antimicrobial layers according to the present disclosure preferably adhere well to the porous flexible foam core and the wound-contact scrim(s).

When contacting a wound site, the antimicrobial layer and/or articles of the present disclosure are hydrated by the tissue fluids and wound exudate. Antimicrobial layers according to the present disclosure comprise polycarboxylic acid chelator compounds that, in an aqueous environment, have antimicrobial properties at an acidic pH. Thus, antimicrobial layers of the present disclosure comprise appropriate quantities of acidic components (e.g., the free acid of the polycarboxylic acid chelator compound) and basic components (e.g., NaOH or a salt of a polycarboxylic acid chelator compound) such that the antimicrobial layer, when mixed well with deionized water at a 1:9 mass ratio, forms an aqueous mixture having a pH of about 2.5 to 5.5. In certain embodiments, the pH of the resulting aqueous mixture is at least 2.5, 3.0, 3.5, 4.0, 4.5, 5.0, or even at least 5.5.

A variety of other ingredients may be added to the antimicrobial layers according to the present disclosure for desired effect. These include, but are not limited to, surfactants, skin emollients and humectants such as, for example, those described in U.S. Pat. No. 5,951,993 (Scholz et al.), fragrances, colorants, and/or tackifiers.

Figure 2:
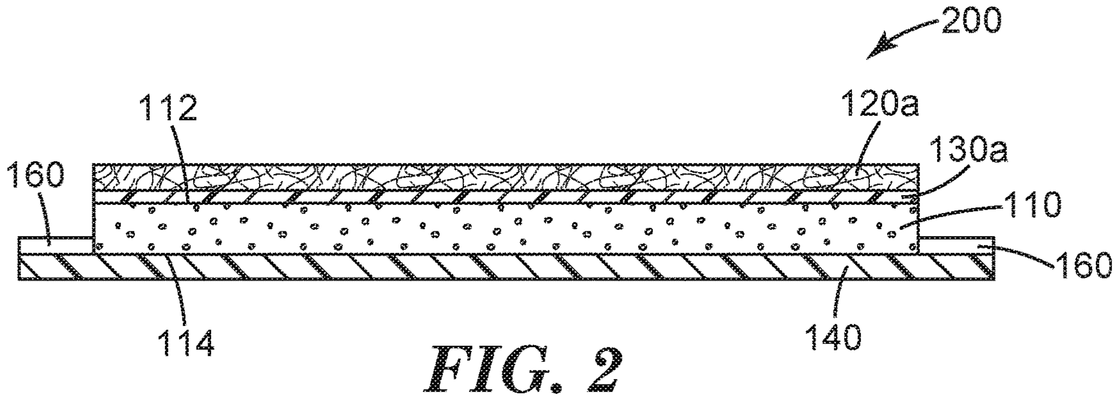
FIG. 2 is a schematic side view of another exemplary wound dressing material 200 according to the present disclosure.

Optionally a flexible adhesive barrier film is adhered to and proximate to the second major side of the porous flexible foam core. Referring now to FIG. 2, wound dressing material 200 comprises porous flexible foam core 110 having first and second opposed major sides (112, 114). First wound-contact scrim 120*a* comprises copolymer fibers comprising divalent hydroxyethylene monomer units and divalent dihydroxybutylene monomer units. First antimicrobial layer 130*a* is sandwiched between first major side 112 of porous flexible foam core 110 and first wound-contact scrim 120*a*. Flexible adhesive barrier film 140 is adhered to and proximate to second major side 114 of porous flexible foam core 110. In the particular embodiment shown, flexible adhesive barrier film 140 extends beyond the periphery of the other components such as the first wound contact scrim 120*a*, first antimicrobial layer 130*a*, and porous flexible foam core 110 so that it may stick to the skin surrounding the wound, however this is not a requirement. In this embodiment, the exposed adhesive side of the adhesive barrier film may be protected by a disposable protective releasable liner 160.

Commercially available suitable flexible adhesive barrier films are marketed by 3M Company under the trade designation TEGADERM (e.g., 3M TEGADERM Transparent Film Roll), by Johnson & Johnson Company, New Brunswick, New Jersey under the trade designation BIOCLUSIVE, and by T. J. Smith & Nephew, Hull, England under the trade designation OP-SITE.

Wound dressing materials according to the present disclosure may have any basis weight, thickness, porosity, and/or density unless otherwise specified. In some embodiments, the wound dressing materials comprise a lofty open nonwoven fiber web.

Wound dressing materials according to the present disclosure may have any desired thickness. In many embodiments, the thickness is in the range of 0.5 to 6 mm, more preferably 0.75 to 5 mm, and more preferably 1 to 4 mm. In many embodiments, the basis weight is in the range of 100 to 1000 grams per square meter (gsm), more preferably 150 to 900 gsm, and more preferably 200 to 800 gsm. Likewise, the porous flexible foam core may have any basis weight, but in many embodiments, it is preferably in the range of 20 to 500 gsm, more preferably 50 to 400 gsm, and more preferably 75 to 300 gsm.

The wound dressing material may be provided in roll form, or it may be converted into sheets or bandages (optionally further comprising a peripheral supporting frame).

Preferably, to maintain a low relative humidity, the wound dressing material should be packaged in a package with a low moisture vapor transmission rate (MVTR) such as, for example, a Techni-Pouch package (Technipaq, Inc., Crystal Lake, Illinois) with a PET/Aluminum Foil/LLDPE material construction.

Wound dressing materials according to the present disclosure can be made by any suitable method, including, for example, sequential or simultaneously pressure and/or heat lamination of the wound-contact scrim(s), antimicrobial layer(s), fiber web, and optional flexible adhesive barrier film. In some embodiments, the antimicrobial layers may be coated (e.g., spray coated, roll coated, curtain coated, or gravure coated), typically with an associated drying step, onto either or both of the wound-contact scrim(s) and the porous flexible foam core. Such manufacturing techniques will be apparent to those of ordinary skill in the art.

Wound dressing materials according to the present disclosure are useful, for example, for covering a wound. Typically, exposed surface of the wound is cleaned and/or treated with antiseptic (if necessary) and then contacted with the first wound-contact scrim of the wound dressing material, although this is not a requirement. In some embodiments, the wound dressing material can be covered with a secondary wound dressing.

Objects and advantages of this disclosure are further illustrated by the following non-limiting examples, but the particular materials and amounts thereof recited in these examples, as well as other conditions and details, should not be construed to unduly limit this disclosure.

EXAMPLES

Unless otherwise noted, all parts, percentages, ratios, etc. in the Examples and the rest of the specification are by weight.

Preparation of Fiber Web 1 (9 gsm)

A melt-blown (blown microfiber, BMF) nonwoven fiber web was made using Nichigo G-Polymer butanediol vinyl alcohol copolymer (BVOH) pellets (obtained as Nichigo G-Polymer OKS 8112 from the Mitsubishi Chemical Corporation, Tokyo, Japan). A conventional melt-blowing process was employed similar to that described in V. A. Wente, "Superfine Thermoplastic Fibers" in *Industrial Engineering Chemistry,* 1956, Vol. 48, pages 1342 et seq. More particularly, the melt-blowing die had circular smooth surfaced orifices, spaced 10 to the centimeter, with a 5:1 length to diameter ratio. Molten (co) polymer was delivered to the die by a 20 mm twin screw extruder (from Steer America, Uniontown, Ohio). The extruder was equipped with two weight loss feeders to control the feeding of the (co) polymer resins to the extruder barrel, and a gear pump to control the (co) polymer melt flow to a die. The extruder temperature was at about 210° C. and it delivered the melt stream to the BMF die, which itself was maintained at 210° C. The gear pump was adjusted so that a 1.0 lb/hour/inch die width (0.18 kg/hour/cm die width) (co) polymer throughput rate was maintained at the die. The primary air temperature of the air knives adjacent to the die orifices was maintained at approximately 325° C. This produced a web on a rotating collector spaced 8.2 cm from the die. The speed of the collector was 26.5 meters/minute. The web had a basis weight of approximately 9 gsm and a fiber diameter range of 5-25 micrometers.

Preparation of Fiber Web 2 (20 gsm)

Fiber web 2 was made in the same manner as fiber web 1 except that the collect speed was 13.9 meters/minute. The web had a basis weight of approximately 20 gsm and a fiber diameter range of 5-25 micrometers.

Preparation of Fiber Web 3 (80 Gsm)

Fiber web 3 was made in the same manner as fiber web 1 except that the collect speed was 3.5 meters/minute. The web had a basis weight of approximately 80 gsm and a fiber diameter range of 5-25 micrometers.

Preparation of Antimicrobial Composition for the Antimicrobial Layer

An antimicrobial composition was prepared in a 100 g batch using the components listed in Table 1. All of the components except the L-PVPK60 were added to a MAX 100 mixing cup (Flacktec Incorporated, Landrum, South Carolina) and mixed at 3500 rpm (revolutions per minute) for 1 minute using a DAC 400 FVZ SPEEDMIXER instrument (Flacktec). The L-PVPK60 aqueous mixture was added to the cup and the contents were mixed for 1 minute at 3500 rpm.

The viscous composition was knife-coated onto a release liner using a gap of 254 micrometers. The coating was then dried at 80° C. for 10 minutes in a convection oven to produce a coating with a basis weight of 100 gsm.

TABLE 1

| COMPONENT | WEIGHT PERCENT | SOURCE |
|---|---|---|
| Glycerol | 19 | Cargill Corporation, Wayzata, Minnesota |
| Linear polyvinylpyrrolidone K60, 47% in water (L-PVPK60) | 50 | Ashland Incorporated, Covington, Kentucky |
| Benzalkonium chloride 50% (BAC) | 0.3 | Novo Nordisk Pharmatech, Koge, Denmark |
| Capryl glycol (Hydrolite 8) | 0.6 | Symrise AG, Holzminden, Germany |
| Sterile water | 12.6 | Rocky Mountain Biologicals, Missoula, Montana |
| Sodium Citrate | 10 | MilliporeSigma, St. Louis, Missouri |
| Citric acid monohydrate | 7.5 | Millipore Sigma |

Example 1

An antimicrobial wound care article with absorbent foam core having a layered construction:

Layer 1:9 gsm BVOH (Fiber web 1)

Layer 2:100 gsm antimicrobial coating

Layer 3: Foam core (SAQ hydrophilic polyurethane foam, standard grade, natural color, 0.5 cm thickness, Crest Foam Industries, Moonachie, New Jersey)

Layer 4:100 gsm antimicrobial coating

Layer 5:9 gsm BVOH (Fiber web 1)

The antimicrobial layer is laminated to each outer surface of the foam material using hand pressure. Then, the release liner is peeled off one of the antimicrobial layers and a section of fiber web 1 is laminated to the other side of the antimicrobial layer using hand pressure. The same process is repeated on the other side. The resulting construction is cut into 4 inch by 4 inch (10 cm×10 cm) articles.

Example 2

An antimicrobial wound care article with absorbent foam core having a layered construction:

Layer 1:20 gsm BVOH (Fiber web 2)

Layer 2:100 gsm antimicrobial coating

Layer 3: Foam core (SAQ hydrophilic polyurethane foam, standard grade, natural color, 0.5 cm thickness, Crest Foam Industries)

Layer 4:100 gsm antimicrobial coating

Layer 5:20 gsm BVOH (Fiber web 2)

This example is identical to Example 1, except the outer layer is 20 gsm BVOH melt-blown fiber.

Example 3

An antimicrobial wound care article with absorbent foam core having a layered construction:

Layer 1:80 gsm BVOH (Fiber web 3)

Layer 2:100 gsm antimicrobial coating

Layer 3: Foam core (SAQ hydrophilic polyurethane foam, standard grade, natural color, 0.5 cm thickness, Crest Foam Industries)

Layer 4:100 gsm antimicrobial coating

Layer 5:80 gsm BVOH (Fiber web 3)

This Example is identical to Example 1, except the outer layer is 80 gsm BVOH melt-blown fiber.

Example 4

Three-layer antimicrobial wound care article with absorbent foam core having a layered construction:

Layer 1:80 gsm BVOH

Layer 2:100 gsm antimicrobial coating

Layer 3: Foam core (SAQ hydrophilic polyurethane foam, standard grade, natural color, 0.5 cm thickness, Crest Foam Industries)

This Example is identical to Example 2, except it only has three layers. The antimicrobial layer and the foam layer are only present on one side of the construction.

Example 5

An antimicrobial wound care article with absorbent foam core having a layered construction:

Layer 1:80 gsm BVOH (Fiber web 3)

Layer 2:100 gsm antimicrobial coating

Layer 3: Foam core (SAQ hydrophilic polyurethane foam, standard grade, natural color, 0.5 cm thickness, Crest Foam Industries)

Layer 4: 3M TEGADERM Transparent Film (from a 3M TEGADERM Transparent Film Roll, 6 inch (15 cm) diameter, 3M Company)

This Example is similar to Example 4, except it contains a transparent 3M TEGADERM Film layer laminated to the construction. This layer is larger than the fiber/antimicrobial layer/foam construction, so that there is a cover and an adhesive border around the absorbent/antimicrobial portion of the construction.

What is claimed is:

1. A wound dressing material comprising: a porous flexible foam core having a first major side opposed to a second major side; a first wound-contact scrim comprising first water-sensitive fibers, wherein the first water-sensitive fibers comprise a first copolymer comprising divalent hydroxyethylene monomer units and divalent dihydroxybutylene monomer units; and a first antimicrobial layer sandwiched between and in direct contact with both the first major side of the porous flexible foam core and the first wound-contact scrim; wherein the first antimicrobial layer comprises at least one antimicrobial compound and at least one polycarboxylic acid chelator compound having an aromatic region and an aliphatic region, wherein the carboxylic acids are disposed upon the aromatic region, the aliphatic region, or any combination thereof; and the at least one polycarboxylic acid chelator compound comprises 3-(2-carboxyphenyl) propionic acid, 3-(4-carboxyphenyl) propionic acid, 4-[(2-carboxyphenyl)amino]benzoic acid, or any combination thereof.

2. The wound dressing material of claim 1, further comprising a flexible adhesive barrier film adhered to and proximate to the second major side of the porous flexible foam core.

3. The wound dressing material of claim 1, further comprising:

a second wound-contact scrim comprising second water-sensitive fibers, wherein the second water-sensitive fibers comprise a second copolymer comprising divalent hydroxyethylene monomer units and divalent dihydroxybutylene monomer units; and a second antimicrobial layer sandwiched between and in direct contact with both the second major side of the porous flexible foam core and the second wound-contact scrim.

4. The wound dressing material of claim 1 wherein the first water-sensitive fibers have an average fiber diameter of 2 to 100 microns.

5. The wound dressing material of claim 1, wherein the first wound-contact scrim further comprises secondary fibers comprising at least one of polyvinyl alcohol, carboxymethyl cellulose, rayon, cotton, cellulose acetate, thermoplastic polyurethane, chitosan, polyacrylic acid, sulfonated cellulose, alginate, or cellulose ethyl sulfonate.

6. The wound dressing material of claim 1, wherein the first wound-contact scrim further comprises secondary fibers comprising at least one of polyethylene, polypropylene, polybutylene, poly (ether ether ketone), poly-4-ethylpentene, polyethylene terephthalate, polyvinyl chloride, polymethyl methacrylate, polyacrylonitrile, a polyamide, a polyester, polystyrene, a styrenic block copolymer, a polyurethane comprising polyethers, a block copolymers of polyether, or polypropylene oxide.

7. The wound dressing material of claim 1, wherein the porous flexible foam core comprises a porous polyurethane foam.

8. The wound dressing material of claim 1, wherein the first copolymer further comprises divalent acetoxyethylene monomer units.

9. The wound dressing material of claim 1, wherein the divalent dihydroxybutylene monomer units comprise divalent 3,4-dihydroxybutan-1,2-diyl monomer units.

10. The wound dressing material of claim 1, wherein the first wound-contact scrim is melt-blown or spunbonded.

11. A method of using a wound dressing material, the method comprising contacting the first wound-contact scrim of the wound dressing material of claim 1 with an exposed surface of a wound.

12. The wound dressing material of claim 1, wherein the at least one antimicrobial compound is selected from the group consisting of antibiotics, chlorhexidine, antimicrobial lipids, phenolic antiseptics, cationic antiseptics, iodine, peroxide antiseptics, antimicrobial natural oils, alkane-1,2-diols having 6 to 12 carbon atoms, silver, silver salts, silver complexes, silver oxide, copper, copper salts, and combinations thereof.

13. The wound dressing material of claim 1, wherein the first antimicrobial layer comprises 5 weight % to 60 weight % of the polycarboxylic acid chelator compound.

14. The wound dressing material of claim 1, wherein the first antimicrobial layer further comprises one or more preservatives.

15. A method of making a wound dressing material, the method comprising laminating sequential layers: a) a first wound-contact scrim comprising water-sensitive fibers, wherein the water-sensitive fibers comprise a first copolymer comprising divalent hydroxyethylene monomer units and divalent dihydroxybutylene monomer units; b) a first antimicrobial layer comprising at least one antimicrobial compound and at least one polycarboxylic acid chelator compound having an aromatic region and an aliphatic region, wherein the carboxylic acids are disposed upon the aromatic region, the aliphatic region, or any combination thereof, and the at least one polycarboxylic acid chelator compound comprises 3-(2-carboxyphenyl) propionic acid, 3-(4-carboxyphenyl) propionic acid, 4-[(2-carboxyphenyl) amino]benzoic acid, or any combination thereof; and c) a porous flexible foam core; wherein the first antimicrobial layer is in direct contact with both the first wound-contact scrim and the foam core.

16. The method of claim 15, wherein the sequential layers further comprise:

d) a second antimicrobial layer; and e) a second wound-contact scrim comprising second water-sensitive fibers, wherein the second water-sensitive fibers comprise a second copolymer comprising divalent hydroxyethylene monomer units and divalent dihydroxybutylene monomer units;

wherein the second antimicrobial layer is in direct contact with both the second wound-contact scrim and the foam core.

17. The method of claim 15, wherein the sequential layers further comprise d) a flexible adhesive barrier film adhered to and proximate to the second major side of the porous flexible foam core.

18. The method of claim 15, wherein the sequential layers are laminated simultaneously.

* * * * *